(12) United States Patent
Persson

(10) Patent No.: US 6,848,909 B1
(45) Date of Patent: Feb. 1, 2005

(54) METHOD AND DEVICE FOR PRODUCING A MODEL FOR A PROSTHESIS IN THE HUMAN BODY

(75) Inventor: Magnus Persson, Buckinghamshire (GB)

(73) Assignee: Nobel Biocare AB, Göteborg (SE)

( * ) Notice: Subject to any disclaimer, the term of this patent is extended or adjusted under 35 U.S.C. 154(b) by 210 days.

(21) Appl. No.: 10/129,444
(22) PCT Filed: Oct. 20, 2000
(86) PCT No.: PCT/SE00/02032
§ 371 (c)(1),
(2), (4) Date: Aug. 23, 2002
(87) PCT Pub. No.: WO01/32092
PCT Pub. Date: May 10, 2001

(30) Foreign Application Priority Data

Nov. 5, 1999 (SE) .............................. 9904019

(51) Int. Cl.[7] .............................................. A61C 13/00
(52) U.S. Cl. ..................................................... 433/213
(58) Field of Search ................................ 433/213, 223, 433/202.1, 201.1, 171; 264/19; 29/896.1

(56) References Cited

U.S. PATENT DOCUMENTS

| | | | | |
|---|---|---|---|---|
| 3,337,956 A | * | 8/1967 | Rene | 433/213 |
| 4,767,331 A | * | 8/1988 | Hoe | 433/213 |
| 5,028,235 A | * | 7/1991 | Smith | 433/223 |
| 5,092,771 A | * | 3/1992 | Tatum, III | 433/173 |
| 5,730,600 A | * | 3/1998 | Shoher et al. | 433/223 |
| 5,813,859 A | * | 9/1998 | Hajjar et al. | 433/223 |

FOREIGN PATENT DOCUMENTS

| | | | | |
|---|---|---|---|---|
| EP | 0490848 | 6/1992 | | |
| EP | 0634150 | 1/1995 | | |
| EP | 0756852 | 2/1997 | | |
| WO | WO99/62422 | * 12/1999 | | A61C/13/00 |

* cited by examiner

Primary Examiner—Todd E. Manahan
(74) Attorney, Agent, or Firm—Venable LLP; Eric J. Franklin

(57) ABSTRACT

A method for producing a model for an oral prosthesis in the human body. A model top part and a model bottom part are selected having oblique assembly surfaces. The model bottom part includes an outer surface that slopes outwards from a bottom surface of the model bottom part. The outer surfaces of different bottom model parts have different maximal heights. The model bottom part and the model top part are arranged in a mutual rotational position in dependence upon a vertical extent of the oral prosthesis in relation to a securement in the bone. The model top part and the model bottom part are put together and anchored to one another by their assembly surfaces. Malleable material is applied to at least a top part of the assembled model top part and bottom part, thereby realizing an outer surface of the oral prosthesis.

21 Claims, 2 Drawing Sheets

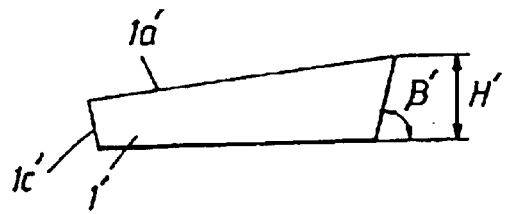
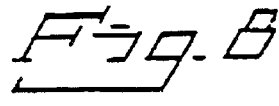
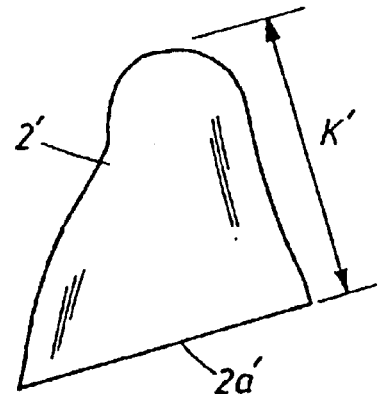
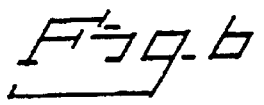
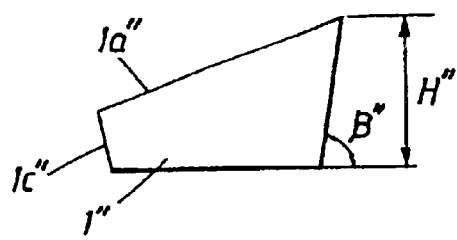
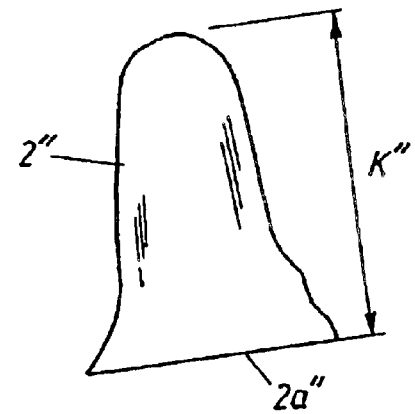
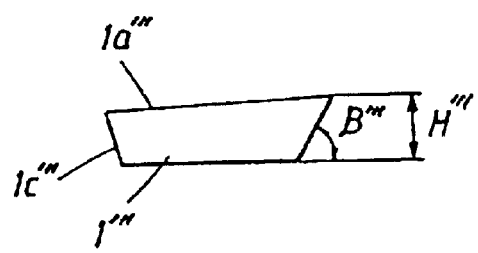
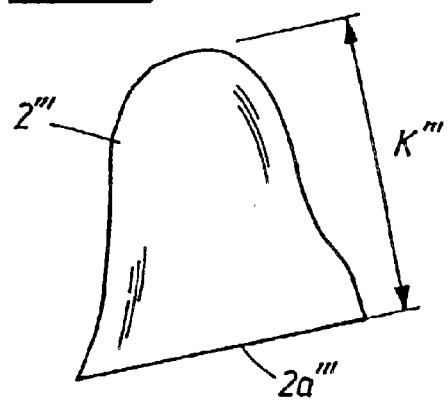

METHOD AND DEVICE FOR PRODUCING A MODEL FOR A PROSTHESIS IN THE HUMAN BODY

FIELD OF THE INVENTION

The present invention relates to a method for producing a model for an oral prosthesis in the human body. The prosthesis is able to constitute a replacement for the whole or parts of one or more teeth. The model is designed to be secured in a rotatable holder, which can be of a known type, and, following securing, to allow its outer surface to be read during rotation through the use of known reading members. The invention also relates to a device for producing such a model.

BACKGROUND OF THE INVENTION

It is previously known to build models for dentures and constructions which are to be applied to tooth remnants, implants, spacers, etc. in the jaw (see SE 98.01933-4) with wax. The prosthesis or the model is configured depending upon the position and construction of the prosthesis in the jaw in relation to the rest of the dental environment. This model-production work is carried out by the dental technician. The production time for the model and the shaping of the model is largely dependent upon the craftsmanship of the dental technician.

SUMMARY OF THE INVENTION

There is a need to create a simplified process for the model production and, in particular, there is a need for clear and simple tools which will facilitate the work and will no longer be so highly dependent upon the craftsmanship of the dental technician. The tools should be easy to use and should enable model production to be speeded up. The invention sets out to solve these problems and proposes the use of a system of tools based on a modular concept for use in production of the model.

Model production should be realized in connection with an individual dental situation and, in addition, should be usable for a variety of system platforms in which different types of implants, fixture systems, tooth remnant mounts, spacers, etc, are present. The invention sets out to solve this problem also.

Model production should be afforded a production facility and structure which takes care of the strength related problems. That is, the model body should have an extent in relation to the direction of securement in the bone, for example the jaw bone, which offers optimal strength and, at the same time, extends in the aesthetically correct direction in the dental situation in question. The invention solves this problem also.

What primarily can be considered to be characteristic of the new method is that the model is made up of top and bottom parts which are chosen from among a small number of prefabricated top and bottom parts or ones which can be produced step-by-step. These top and bottom parts are put together and anchored to one another by mutually assigned, oblique assembly surfaces. The bottom parts are constructed with outer surfaces which slope outwards 2% from the bottom, that is, from the securement surface, and have mutually different angles of inclination exceeding a predetermined angular value and have different maximal or peak heights. The new method is additionally characterized in that the choice of top and bottom parts and their mutual rotational position in the assembly depends upon the vertical extent of the prosthesis in relation to a securement in the bone and in that malleable material, preferably constituted by wax, is applied to at least the top part of the top and bottom parts put together in this way, by means of which material the final external shape and the outer surface of the model are realized.

In a refinement of the new method, the said top and/or bottom parts are constructed of material which allows the part concerned to be ground at its respective outer edges to achieve an expedient model frame.

What primarily can be considered to be characteristic of the new device is that it comprises a small number of modular units which can be put together and which, in the respective assembly of a model, form top and bottom parts of the model. The modular units have oblique mating surfaces by means of which the respective assembly can be realized. The bottom parts in question are further arranged with surfaces which slope outwards from the bottom, that is, from the bottom side or base surface of the model, and in which the angle of inclination and the maximal or peak height are different on the different bottom parts. Finally, the new device is characterized in that the respective assembly of the top and bottom parts forms a model frame in which at least the top part or top parts can be allocated malleable material, preferably constituted by wax, by means of which material the final external shape and the outer surface of the model can be realized.

In refinements of the inventive concept, the respective bottom part is constructed with a base part or base surface, by means of which the model can be applied to the holder. The outwardly inclined outer surfaces extend at angles of inclination which, for reading related reasons, must exceed ca. 50°. In one embodiment, three or four different bottom parts and three to four different top parts are used in the modular system, which can be put together in pairs to form the respective model frame. The number of top and bottom parts does not need to be identical and by the term "small number" is here meant the number of three to four different parts. A preferred embodiment is constituted by the fact that, in the respective frame constructed with modular units, top and bottom parts are fixed to one another by means of glue applied to the oblique surfaces, which glue, by way of example, can here be constituted by cyan acrylate. In the respective model frame, the top and bottom parts can be applied to one another in a mutual rotational-angle relationship relative to the directional axis of the model. The differences between the angle of inclination of the different bottom parts can in one embodiment assume values of around ca. 10°. The peak height measurements of the different bottom parts can differ, for example, by ca. 1–2 mm. In addition, the oblique mating surfaces can be arranged with different angles in relation to the base surface of the respective bottom part.

The above-proposed allows a substantially simplified production process for models of this type comprising modular units, in which the time gain for production of the model in question can amount to 20–50% in relation to the model produced manually only using wax. The new system requires only a small number of modular units which, per se, can be constructed in a suitable material which can easily be worked in connection with the putting-together of the frame parts of the model. As a result of the proposed, it is possible simply and easily to assemble a model frame which offers the most advantageous extent in terms of strength, at the same time as the model frame acquires an extent or direction in relation to the bone securement which meets the prosthodontal and aesthetic requirements. From the small number of modular units, it is easy for the dental technician to choose the top and bottom parts to be used for the dental or corresponding situation in question. The application of the malleable material to the outside of the model frame is a relatively simple process compared with the model having to be constructed on the basis of wax modelling as in the past.

BRIEF DESCRIPTION OF THE DRAWINGS

A currently proposed method and a device which have the characteristics indicative of the invention shall be described below with simultaneous reference to the appended drawings, in which:

FIGS. 5–7 show from the side and in basic representation embodiments of various bottom parts included in the modular system, and FIGS. 8–10 show from the side and in basic representation various embodiments of top parts which will be able to be applied to bottom parts corresponding to those according to FIGS. 5–7.

DETAILED DESCRIPTION OF THE PREFERRED EMBODIMENTS

Figure 1:
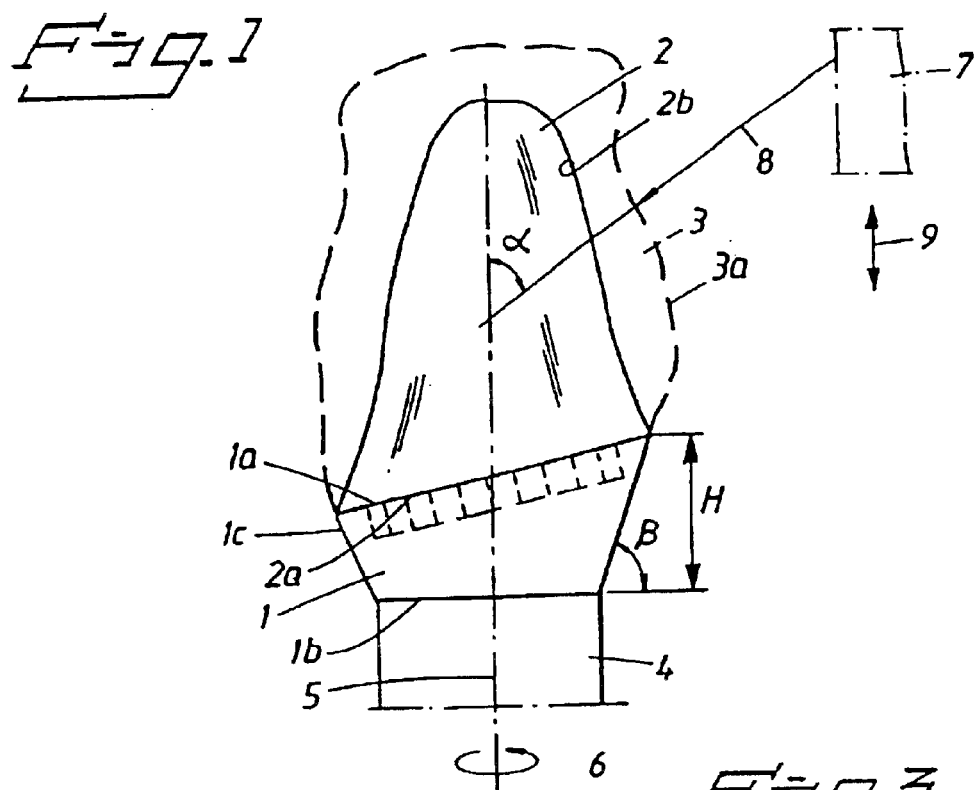
FIG. 1 shows in vertical view and in basic representation a configuration of the model which is connectable to a symbolically represented holder of a type which is known per se and in which the outer surface of the model is scannable by means of a scanning apparatus which, per se, is basically defined.

In FIG. 1, a model frame is constructed from a bottom part 1 and a top part 2 applied thereto. The bottom part has an oblique top surface 1$a$ and the top part has an interacting, oblique bottom surface 2$a$. For example, the top surface can have a protruding male part and the bottom surface a corresponding female part, this having been marked in diagrammatic representation in FIG. 1. At least the top part 2 is coated on its outer surface 2$b$ with a malleable material 3, which can be constituted by wax or equivalent of a type which is known per se. The model is thus formed by the bottom part 1 and top part 2 and the wax coating 3. The model can be applied to a holder 4 of a type which is known per se via a bottom surface 1$b$ on the bottom part. The holder is arranged such that it is rotatable in a known manner about a rotational axis 5 for the holder and the model. An arrow showing rotation about the axis 5 is indicated by 6. The outer surface 3$a$ of the model will be read with a reading apparatus 7, which can be of a type which is known per se. The reading direction is indicated by 8 and extends at an angle $\alpha$ in relation to the rotational axis 5. During the reading, the reading apparatus 7 and the model 3 and the holder are acted upon one relative to the other, which has been symbolized by the vertical directional arrows 9.

The bottom part 1 is provided with a side surface 1$c$ sloping outwards from the base surface 1$b$. The angle of inclination has been indicated by $\beta$ in FIG. 1. In order with the obliquely incident reading direction 8, to achieve an expedient reading of the whole surface of the model, which surface, in addition to the surface 3$a$, also consists of the surface 1$c$, the angle of $\beta$ must not be less than ca. 50 in the present case. In FIG. 1, a peak or maximal height of the inclined surface is indicated by H. The surfaces 1$a$ and 2$a$ are obliquely inclined in relation to the base surface 1$b$.

In FIG. 1, the body for the top part 2 is arranged essentially concentrically about the rotational axis 5. According to the invention, the body can, however, be given a different direction.

Figure 2:
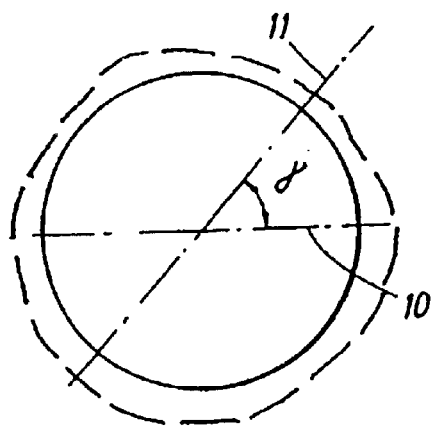
FIG. 2 shows from above the model according to FIG. 1.

According to FIG. 2, the angle of rotation $\gamma$ between the top and bottom parts is varied in order to achieve different extents for the vertical extent of the top part in relation to the vertical extent of the bottom part. In FIG. 2, a first diametric axis is indicated by 10. This diametric axis can be considered to be assignable to the rotational position of the bottom part. In addition, a second diametric axis 11 is shown, which is assignable to the rotational angle position of the top part relative to the bottom part. By adjusting the angle $\gamma$ between the diametric axes 10 and 11, different relative directions can thus be obtained between the top and bottom parts.

Figure 3:
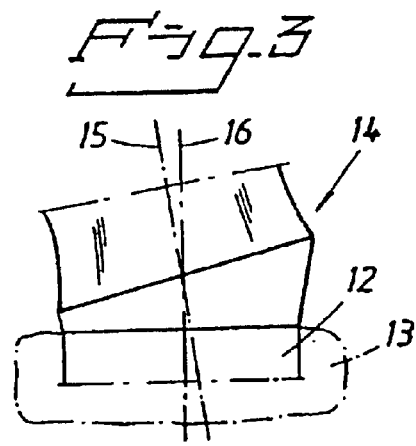
FIG. 3 shows in vertical view and in basic representation a first dental situation, in which the prosthesis is applied to a fixture system in a partially shown jawbone.

In FIG. 3, a fixture is symbolized by 12 and a tooth bone or jawbone by 13. The prosthesis in question has been symbolized by 14 and in certain cases the extent (vertical extent) 15 of the prosthesis may need to differ from the extent 16 of the implant in relation to the jawbone 13. The invention enables models to be produced which are representative of the differences.

Figure 4:
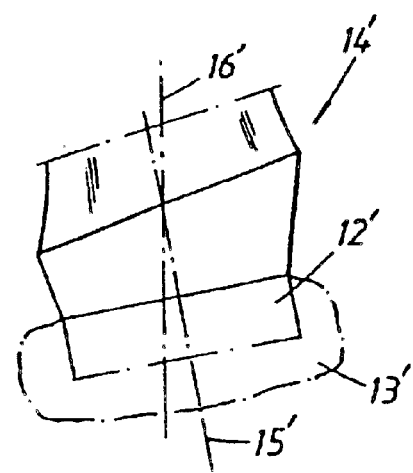
FIG. 4 shows in vertical view and in basic representation a case which is distinct from the case according to FIG. 3, in which the prosthesis is to be connected with a different extent in relation to the extent of the bone securement.

In FIG. 4, the implant 12' is shown obliquely inclined in the jawbone 13'. The longitudinal axis 15' of the implant can in this case be considered to be angled in relation to the extent 16' in which the dental prosthesis 14' may be considered to extend. The new model-production process can provide for this case also. FIGS. 5–10 show examples of a modular system according to the invention. In FIGS. 5, 6 and 7, the bottom parts 1', 1" and 1'" are shown, which are configured with different angles of inclination $\beta$', $\beta$", and $\beta$'" respectively and different peak or maximal heights H', H" and H'" respectively. The bottom parts 1', 1" and 1'" are constructed with different inclining outer surfaces 1$c$', 1$c$' and 1$c$'" respectively, arranged to correspond to different types of fixture design.

According to FIGS. 8, 9 and 10, the top parts 2', 2" and 2'" are provided with different configurations and different inclinations of the bottom parts 2$a$', 2$a$" and 2$a$'" respectively and different heights K', K" and K'" respectively. The parts according to FIGS. 5–10 will be able to be put together according to choice in order to comply with the production of models for different dental situations. In certain cases, grinding of the parts is carried out. The parts are therefore made in grindable material, for example plastic, metal, alloy (light-bound), wax, etc., the top and bottom parts are put together with glue (fast-acting glue) of suitable type, for example cyan acrylate.

The invention is not limited to the embodiment shown above by way of example, but can be subject to modifications within the scope of subsequent patent claims and the inventive concept.

What is claimed is:

1. A method for producing a model for an oral prosthesis in the human body, the method comprising:
    selecting a model top part and a model bottom part having oblique assembly surfaces, wherein the model bottom part includes an outer surface that slopes outwards from a bottom surface of the model bottom part, and wherein the outer surfaces of different bottom model parts have different maximal heights;

arranging the model bottom part and the model top part in a mutual rotational position in dependence upon a vertical extent of the oral prosthesis in relation to a securement in the bone;

putting together and anchoring the model top part and the model bottom part to one another by their assembly surfaces; and applying malleable material to at least a top part of the assembled model top part and model bottom part, thereby realizing an outer surface of the oral prosthesis.

2. The method according to claim 1, wherein the model top part and the model bottom part are selected from among prefabricated top and bottom parts.

3. The method according to claim 1, wherein the model top part and model bottom part can be produced step by step.

4. The method according to claim 1, further comprising:

securing the model in a rotatable holder;

rotating the model; and reading an outer surface of the model during rotation.

5. The method according to claim 1, wherein the prosthesis comprises a prosthesis for at least a portion of at least one tooth.

6. The method according to claim 1, wherein the mutually different angles of inclination exceed about 50°.

7. The method according to claim 1, wherein the malleable material comprises wax.

8. The method according to claim 1, further comprising:

grinding an outer edge of the model top part and the model bottom part prior to applying the malleable material.

9. A device operative to produce a model for an oral prosthesis in the human body, the device comprising:

an assembly comprising modular units including a model top part and a model bottom part having oblique assembly surfaces, wherein the model bottom part includes an outer surface that slopes outwards from a bottom surface of the model bottom part, wherein the outer surfaces of different bottom model parts have different maximal heights, the assembled model top part and model bottom part comprising a model frame;

malleable material arranged on at least a top part of the model frame, the malleable material forming at least a portion of an outer surface of the model.

10. The device according to claim 9, further comprising:

a rotatable holder that the model is applied in or to, wherein when applied in or to the holder an outer surface of the model is exposed to reading during rotation.

11. The device according to claim 9, wherein the oral prosthesis comprises at least a part of at least one tooth or spacer.

12. The device according to claim 9, wherein the malleable material comprises wax.

13. The device according to claim 9, wherein the model bottom part comprises a base surface, by means of which the model can be applied to or in the holder, and wherein a respective outwardly inclined outer surface extends at an angle of inclination that exceeds about 50°, thereby permitting reading with a reading angle in relation to the rotational axis of the holder and of the model.

14. The device according to claim 9, wherein the modular units comprise three or four different bottom parts, corresponding to different types of fixture design, and three or four different top parts, which can be put together in pairs to form the respective model frame.

15. The device according to claim 9, wherein the model top part and model bottom part are fixed to one another with glue applied to the oblique assembly surfaces.

16. The device according to claim 9, wherein the glue is cyan acrylate.

17. The device according to claim 16, wherein the glue comprises cyan acrylate.

18. The device according to claim 9, wherein the top and bottom parts in the model frame can be applied to one another in a mutual rotational-angle relationship about a rotational axis of the model.

19. The device according to claim 9, wherein the outer surfaces of different model bottom parts are inclined at angles that differ by about 10°.

20. The device according to claim 9, wherein the maximal heights differ by about 1–2 mm.

21. The device according to claim 9, wherein the oblique assembly surfaces are arranged at different angles in relation to a base surface of the model bottom part.

* * * * *